(12) United States Patent  
Muthukumar et al.

(10) Patent No.: US 8,758,802 B2
(45) Date of Patent: Jun. 24, 2014

(54) METHODS OF INHIBITING CATARACTS AND PRESBYOPIA

(75) Inventors: Murugappan Muthukumar, Amherst, MA (US); Zhaoyang Ou, Webster, NY (US); Deniz Civay, Rensselaer, NY (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 13/514,185

(22) PCT Filed: Dec. 13, 2010

(86) PCT No.: PCT/US2010/060044
§ 371 (c)(1),
(2), (4) Date: Aug. 29, 2012

(87) PCT Pub. No.: WO2011/075430
PCT Pub. Date: Jun. 23, 2011

(65) Prior Publication Data
US 2012/0321675 A1 Dec. 20, 2012

Related U.S. Application Data

(60) Provisional application No. 61/286,139, filed on Dec. 14, 2009, provisional application No. 61/350,161, filed on Jun. 1, 2010.

(51) Int. Cl.
*A61K 31/00* (2006.01)
(52) U.S. Cl.
USPC ........................................................ 424/427
(58) Field of Classification Search
None
See application file for complete search history.

(56) References Cited

U.S. PATENT DOCUMENTS

| | | | |
|---|---|---|---|
| 4,351,826 A | 9/1982 | Clark et al. | |
| 4,620,979 A * | 11/1986 | Schachar | 424/678 |
| 4,665,089 A | 5/1987 | Siezen et al. | |
| 4,771,036 A | 9/1988 | Pigiet et al. | |
| 4,808,182 A * | 2/1989 | Barrett | 623/6.6 |
| 5,055,291 A | 10/1991 | Lam et al. | |
| 5,091,421 A | 2/1992 | Clark et al. | |
| 5,227,382 A | 7/1993 | Aziz et al. | |

(Continued)

FOREIGN PATENT DOCUMENTS

| | | | |
|---|---|---|---|
| CN | 1093259 A | * | 10/1994 |
| CN | 1621091 | | 6/2005 |

(Continued)

OTHER PUBLICATIONS

International Search Report and Written Opinion; International Application No. PCT/US2010/060044; International Filing Date Dec. 13, 2010; Date of Mailing Feb. 28, 2011; 14 pages.

(Continued)

*Primary Examiner* — Anand Desai
*Assistant Examiner* — Melissa Mercier
(74) *Attorney, Agent, or Firm* — Cantor Colburn LLP

(57) ABSTRACT

Described herein are methods of inhibiting or reversing the progression of cataract formation or presbyopia in an eye by administering a $\beta_L$-crystallin electrostatic interaction inhibitor. Both presbyopia and cataracts are caused by aggregation of the soluble crystalline lens proteins called the crystallins, particularly $\beta_L$-crystallin. It has been found that the aggregation of $\beta_L$-crystallin is an electrostatic phenomenon and that electrostatic interaction inhibitors can be employed to prevent the formation of $\beta_L$-crystallin aggregates as well as to deaggregate already formed aggregates.

16 Claims, 7 Drawing Sheets

(56) References Cited

U.S. PATENT DOCUMENTS

| | | |
|---|---|---|
| 5,338,545 A | 8/1994 | Clark et al. |
| 5,658,592 A | 8/1997 | Tanihara et al. |
| 5,756,672 A | 5/1998 | Builder et al. |
| 6,027,745 A | 2/2000 | Nakada et al. |
| 6,103,756 A | 8/2000 | Gorsek |
| 6,294,518 B1 | 9/2001 | Potter et al. |
| 6,835,394 B1 | 12/2004 | Discher et al. |
| 6,945,971 B1 | 9/2005 | Gwon |
| 6,958,224 B2 | 10/2005 | Kumar et al. |
| 2003/0130324 A1 | 7/2003 | McAvoy et al. |
| 2004/0120967 A1 | 6/2004 | Calvani |
| 2005/0079197 A1 | 4/2005 | Kataoka et al. |
| 2005/0249821 A1 | 11/2005 | Paul, Jr. |
| 2005/0260259 A1 | 11/2005 | Bolotin |
| 2008/0227700 A1 | 9/2008 | Ghosh et al. |

FOREIGN PATENT DOCUMENTS

| | | |
|---|---|---|
| CN | 1660920 | 8/2005 |
| CN | 202172410 | 9/2011 |
| CN | 102579353 A | 7/2012 |
| DE | 3906311 A1 | 8/1990 |
| IN | 208748 A1 | 5/2007 |
| JP | 2004161731 | 6/2004 |
| KR | 2010000203 | 1/2010 |
| WO | 9200748 A1 | 1/1992 |
| WO | 9514482 A1 | 6/1995 |
| WO | WO 9514482 A1 * | 6/1995 |
| WO | 9524899 A1 | 9/1995 |
| WO | 0071723 A2 | 11/2000 |
| WO | 0248190 A1 | 6/2002 |
| WO | WO 0248190 A1 * | 6/2002 |
| WO | 03003073 A1 | 1/2003 |
| WO | 2005117987 A1 | 12/2005 |
| WO | 2007025763 A2 | 3/2007 |
| WO | 2009051223 A1 | 4/2009 |
| WO | 2010065024 A1 | 6/2010 |
| WO | 2010130638 A1 | 11/2010 |
| WO | 2012109975 A1 | 8/2012 |

OTHER PUBLICATIONS

Qian, et al.; "Effects of Anionic Surfactant SDS on the Photophysical Properties of Two Fluorescent Molecular Sensors"; Journal of Photochemistry and Photobiology A: Chemistry 200; pp. 402-409; (2008).

Wang et al.; "Safety and Efficacy of Intracapsular Tranilast Microspheres in Experimental Posterior Capsule Opacification"; J Cataract Refract Surg; 33; pp. 21-22-2128; (2007).

International Preliminary Report on Patentability; International Application No. PCT/US2010/06044; International Filing Date Dec. 13, 2010; Date of Mailing Jun. 28, 2012; 9 pages.

IN 208748 A1, May 5, 2007, "Composition for Treatment of Cataract"; Rpendra et al.; English Abstract only; 1 page.

PEGylation Reagents (linkers, crosslinkers and labels)_Products Description; by Uptima; uptima@interchim.com; printer Nov. 30, 2012; 12 pages.

Wang et al.; "Safety and Efficacy of Intracapsular Tranilast Microspheres in Experimental Posterior Capsule Opacification"; Journal Cataract and Refractive Surgery; 33; pp. 2122-2128; (2007).

\* cited by examiner

Proposed Model

METHODS OF INHIBITING CATARACTS AND PRESBYOPIA

CROSS-REFERENCE TO RELATED APPLICATIONS

This application is a 371 of PCT/US2010/060044 filed Dec. 13, 2010, which claims the benefit of priority to U.S. provisional application Nos. 61/286,139, filed on Dec. 14, 2009; and 61/350,161, filed on Jun. 1, 2010, under provisions of 35 U.S.C. 119 and the International Convention for the protection of Industrial Property, which are incorporated herein by reference.

FIELD OF THE INVENTION

The present invention relates to methods of inhibiting or reversing the progression of age related changes in the crystalline lens of an eye.

BACKGROUND

The crystalline lens of the eye is a transparent structure that is suspended immediately behind the iris, which brings rays of light to a focus on the retina. The lens contains both soluble and insoluble proteins; together they constitute 35 percent of the wet weight of the lens. In a young, healthy lens, the soluble proteins, commonly referred to as crystallins, constitute 90 percent of the lens proteins. During the aging process, the lens crystallins form insoluble aggregates, which, at least in part, account for the decreased deformability of the lens nucleus, which characterizes presbyopia, the loss of the eye's ability to change focus to see near objects. The formation of insoluble aggregates of lens crystallins in presbyopia is believed to be an early stage in the formation of age-related cataracts.

Cataracts are defined by cloudiness or opacification in the crystalline lens of the eye. As an individual ages, cataracts form as the crystallins present in the lens are converted into aggregates, resulting in increased lens opacity. Specifically, there is a progressive decrease in the concentration of the soluble chaperone, α-crystallin, in human lens nuclei with age, as it becomes incorporated into high molecular weight aggregates and insoluble protein. The presence of aggregates compromises the health and function of the lens and left untreated, cataracts can lead to substantial vision loss or even blindness. Presently, the most common treatment for cataracts is surgery.

Crystallins are structural proteins most highly expressed in the lens fiber cells of the vertebrate eye. The crystallins are divided into two subfamilies: the α-crystallins (αA and αB) which are members of the small heat shock protein superfamily, also functioning as molecular chaperones; and the evolutionarily-linked superfamily of β- and γ-crystallins which comprise the majority of soluble protein in the lens, and contribute to the transparency and refractive properties of lens structure. In addition to their role in cataract development, αA-crystallin and αB-crystallin have been implicated in neurodegenerative diseases, like Alexander's disease, Creutzfeldt-Jacob disease, Alzheimer's disease and Parkinson's disease.

U.S. Patent Application 2008/0227700 describes deaggregation of proteins using peptides having chaperone activities as a therapeutic treatment. Specifically, αB peptides were used to deaggregate pH-induced aggregates of β-crystallin as measured by light scattering. Provision of a continuous supply of alpha crystallins into the lens is a challenge. What is needed are alternative methods suitable for the deaggregation of crystallins for the inhibition and/or reversal of cataracts and presbyopia.

SUMMARY

In one embodiment, a method of inhibiting or reversing the progression of cataract formation in an eye comprises contacting the eye with an effective cataract-inhibiting amount of an ophthalmic composition comprising at least one $\beta_L$-crystallin electrostatic interaction inhibitor, wherein the electrostatic interaction inhibitor is not a polypeptide.

In another embodiment, a method of inhibiting or reversing the progression of presbyopia in an eye comprises contacting the eye with an effective presbyopia-inhibiting amount of an ophthalmic composition comprising at least one $\beta_L$-crystallin electrostatic interaction inhibitor, wherein the electrostatic interaction inhibitor is not a polypeptide.

In another embodiment, a method of inhibiting or reversing the progression of age related degeneration of a crystalline lens in an eye comprises contacting the eye with an effective degeneration-inhibiting amount of an ophthalmic composition comprising at least one $\beta_L$-crystallin electrostatic interaction inhibitor, wherein the electrostatic interaction inhibitor is not a polypeptide.

Figure 1:
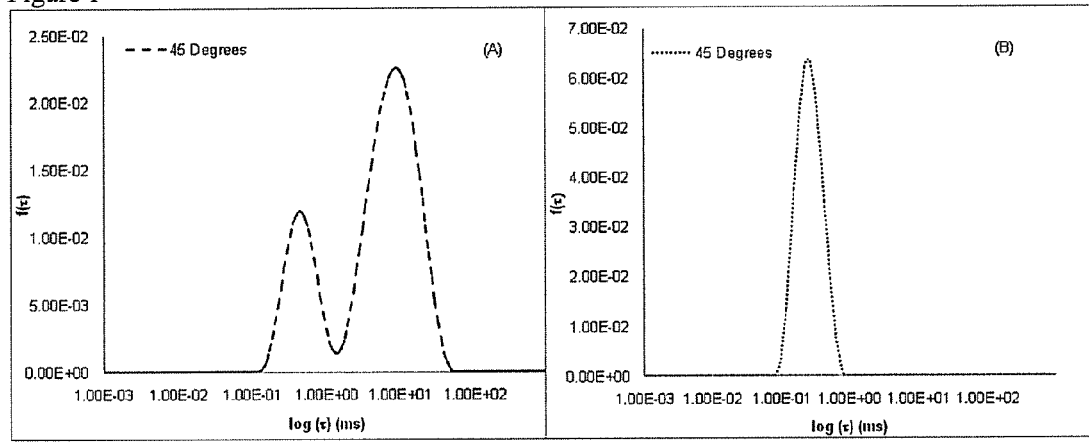
FIG. 1 shows the probability distribution functions produced by dynamic light scattering of (A) 0.2 mg/mL $\beta_L$-crystallin in water and (B) 0.2 mg/mL α-crystallin in water at 23° C., where τ is the lag time.

The above-described and other features will be appreciated and understood by those skilled in the art from the following detailed description, drawings, and appended claims.

DETAILED DESCRIPTION

Disclosed herein are methods of disaggregating a $\beta_L$-crystallin aggregate comprising contacting the $\beta_L$-crystallin aggregate with a composition comprising a $\beta_L$-crystallin electrostatic interaction inhibitor in an amount sufficient to desegregate the $\beta_L$-crystallin aggregates. Further disclosed are methods of inhibiting or reversing the progression of cataract formation in an eye which comprises contacting the eye with an effective cataract-inhibiting amount of a composition comprising a $\beta_L$-crystallin electrostatic interaction inhibitor. Also disclosed are methods of inhibiting or reversing the progression of presbyopia in an eye which comprises contacting the eye with an effective presbyopia-inhibiting amount of a composition comprising a $\beta_L$-crystallin electrostatic interaction inhibitor. In specific embodiments, the electrostatic interaction inhibitor is not a polypeptide.

The inventors herein have employed techniques such as dynamic light scattering, turbidity measurements and transmission electron microscopy to study the aggregates formed by crystallins in solution. Interestingly, while $\alpha$-crystallin in solution exists as a narrow population with a hydrodynamic radius of approximately 10 nm, $\beta_L$-crystallin in solution exists as two populations, one with a hydrodynamic radius of approximately 7 nm and a second population with a hydrodynamic radius of approximately 150 nm. The $\beta_L$-crystallin population with a hydrodynamic radius of about 150 nm is an aggregated population. Further, when $\alpha$-crystallin is added to $\beta_L$-crystallin at a ratio of about 3:1, the aggregated $\beta_L$-crystallin population disappears due to the chaperone nature of $\alpha$-crystallin. In view of the ability to ascertain different populations of $\beta_L$-crystallin, the inventors undertook experiments to identify interaction inhibitors in addition to $\alpha$-crystallin that can reduce the size of or prevent the formation of $\beta_L$-crystallin. It was found that addition of about 0.15 M NaCl decreases $\beta_L$-crystallin aggregate size, while 0.1 mg/Ml sodium dodecyl sulfate has no effect on $\beta_L$-crystallin aggregate size and 0.1 mg/ML proteoglycan results in an increase in $\beta_L$-crystallin aggregate size. In addition, as pH decreases from about pH 10 to about pH 2, the size of $\beta_L$-crystallin aggregates increases.

Without being held to theory, it is believed that the aggregation of $\beta_L$-crystallin is an electrostatic phenomenon. Species such as salts that can disrupt electrostatic interactions can substitute for the chaperone activity of $\alpha$-crystallin and prevent/reduce $\beta_L$-crystallin aggregate size. While sodium dodecyl sulfate is often effective in disrupting protein-protein interactions, it does not reduce $\beta_L$-crystallin aggregate sizes. It is believed that this is because these additives complex with the hydrophobic residues of the crystallin molecules. Even more surprisingly, proteoglycan, increases the size of $\beta_L$-crystallin aggregates. For the case of proteoglycans, many crystallin molecules are believed to noncovalently attach to the proteoglycan molecule which is very large in comparison with the crystallin molecules.

Treatment with $\beta_L$-crystallin electrostatic interaction inhibitors can be used to treat diseases and/or conditions resulting from aggregation of $\beta_L$-crystallin such as cataracts and presbyopia. As used herein, a cataract is an opacity of the crystalline lens of the eye caused by altered protein interactions in the lens. Protein interactions include misfolding of proteins as well as protein-protein interactions such as aggregation. Presbyopia is the impairment of vision due to advancing years or old age. Symptoms of presbyopia include decreased focusing ability for near objects, eyestrain, difficulty reading fine print, fatigue while reading or looking at an illuminated screen, difficulty seeing clearly up close, less contrast when reading print, need for brighter and more direct light for reading, needing to hold reading material further away in order to see it clearly, and headaches, especially headaches when using near vision. Individuals suffering from presbyopia may have normal vision, but the ability to focus on near objects is at least partially lost over time, and those individuals come to need glasses for tasks requiring near vision, such as reading. Presbyopia affects almost all individuals over the age of 40 to a greater or lesser degree.

In the method of inhibiting the progression of cataract formation in an eye, the eye may already contain one or more developing or fully developed cataracts before it is contacted with the $\beta_L$-crystallin electrostatic interaction inhibitor. Accordingly, the method can be used to inhibit the formation of further cataracts in the eye, or to inhibit the formation of mature cataracts from the developing cataracts already present in the eye. Alternatively, the eye may be free of any developing or fully developed cataracts before it is contacted with the $\beta_L$-crystallin electrostatic interaction inhibitor.

In the method of reversing the progression of cataract formation in an eye, at least partial to full reversal of cataracts in the eye is achieved by contacting the eye with a $\beta_L$-crystallin electrostatic interaction inhibitor as disclosed herein.

Similarly, in the method of inhibiting the progression of presbyopia in an eye, the individual may already be experiencing one or more symptoms of presbyopia before the eye is contacted with the $\beta_L$-crystallin electrostatic interaction inhibitor. Accordingly, the method can be used to reduce the progression of the symptom(s) experienced, or to inhibit the formation of additional symptoms of presbyopia. Alternatively, the eye may be free of any symptoms of presbyopia before it is contacted with the $\beta_L$-crystallin electrostatic interaction inhibitor.

In the method of reversing the progression of presbyopia in an eye, at least partial to full reversal of the symptoms of presbyopia in the eye is achieved by contacting the eye with a $\beta_L$-crystallin electrostatic interaction inhibitor as disclosed herein.

As used herein, a $\beta_L$-crystallin electrostatic interaction inhibitor is a molecule suitable to interfere with $\beta_L$-crystallin electrostatic protein-protein interactions which lead to $\beta_L$-crystallin aggregation. In one embodiment, the electrostatic interaction inhibitor is not a polypeptide. $\beta_L$-crystallin electrostatic interaction inhibitors prevent $\beta_L$-crystallin aggregates from forming and/or reduce the size of pre-formed aggregates. In specific embodiments, the $\beta_L$-crystallin electrostatic interaction inhibitor is a salt such as an organic salt, an inorganic salt, or an ionic liquid; and/or a solution having a pH of about 9 to about 5.

In one embodiment, a $\beta_L$-crystallin electrostatic interaction inhibitor comprises at least one salt. The term "salt" as used herein, is intended to include an organic or inorganic salt, including but not limited to one or more of NaCl, KCl, ammonium halides such as $NH_4Cl$, alkaline earth metal halides such as $CaCl_2$, sodium acetate, potassium acetate, ammonium acetate, sodium citrate, potassium citrate, ammonium citrate, sodium sulphate, potassium sulphate, ammonium sulphate, calcium acetate or mixtures thereof. Additional organic salts include alkylammonium salts such as ethylammonium nitrate, sodium citrate, sodium formate, sodium ascorbate, magnesium gluconate, sodium gluconate, tromethamine hydrochloride, sodium succinate, and combinations thereof.

In another embodiment, the $\beta_L$-crystallin electrostatic interaction inhibitor comprises at least one ionic liquid. Ionic liquids are salts composed of organic cations and inorganic or organic anions that are liquid below 100° C. Exemplary ionic liquids include, for example, N'-alkyl and N'-(ω-hydroxyalkyl)-N-methylimidazolium chlorides, triisobutyl(methyl) phosphonium p-toluenesulfonate, 1-ethyl-3-methylimidazolium tetrafluoroborate, 1-butyl-3-methylimidazolium chloride, 1-hexyl-3-methylimidazolium chloride, 1-ethyl-3-methylimidazolium trifluoromethanesulfonate, 1-ethyl-3-methylimidazolium trifluoromethanesulfonate, tetraethylammonium bromide, n-butylpyridinium chloride, tetrabutylphosphonium bromide, benzyltriethylammonium chloride, 1-ethyl-3-methylimidazolium chloride, 1-butyl-2,3-dimethylimidazolium tetrafluoroborate, 1,3-dimethylimidazolium methyl sulfate, 1-butyl-3-methylimidazolium trifluoroacetate, 1-butyl-3-methylimidazolium chloride, 1-butyl-3-methylimidazolium 2(2-methoxyethoxy)ethylsulfate, 1-butyl-1-methylpyrollidinium dihydrogenphosphate, and combinations thereof.

In specific embodiments, the organic salts and ionic liquids contain a cation and an anion, wherein the cation and the anion are each independently an aliphatic group with the length of the aliphatic moiety of four to fifteen carbon atoms.

In another embodiment, the $\beta_L$-crystallin electrostatic interaction inhibitor is a solution having a pH of about 9 to about 5. Typically, the solution will comprise one or more pH regulators such as, for example, sodium hydroxide, potassium hydroxide, sodium carbonate, citric acid, phosphoric acid, acetic acid, and hydrochloric acid.

In one embodiment, the $\beta_L$-crystallin electrostatic interaction inhibitor is not a polypeptide. "Polypeptide", "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The $\beta_L$-crystallin electrostatic interaction inhibitors are contacted with the eye to inhibit the progression of cataracts and/or reduce existing cataracts, or to inhibit and/or reduce the symptoms of presbyopia. As used herein, the term "contacting the eye" encompasses methods of directly applying the $\beta_L$-crystallin electrostatic interaction inhibitor to the eye, that is, the crystalline lens of the eye is contacted with the $\beta_L$-crystallin electrostatic interaction inhibitor in situ in the eye. In the above-described method, suitable means known to those of ordinary skill in the art may be used to contact the eye with the compound. Examples of such methods include, but are not limited to, the compound being injected into the eye, or being dropped or sprayed into the eye, applied in the form of an ophthalmic device, or otherwise topically applied to the eye.

As used herein, the term "effective cataract-inhibiting amount" means an amount which will inhibit the progression or formation of cataracts in an eye or inhibit the progression or formation of mature cataracts from developing cataracts already present in the eye. The effective cataract-inhibiting amount of the $\beta_L$-crystallin electrostatic interaction inhibitor will depend on various factors known to those of ordinary skill in the art. Such factors include, but are not limited to, the size of the eye, the number and progression of any fully developed or developing cataracts already present in the eye, and the mode of administration. The effective cataract-inhibiting amount will also depend on whether the pharmaceutical composition is to be administered a single time, or whether the pharmaceutical composition is to be administered periodically, over a period of time. The period time may be any number of days, weeks, months, or years. In one embodiment, the effective cataract-inhibiting amount of the $\beta_L$-crystallin electrostatic interaction inhibitor is about 0.001 g to about 0.1 g. Specifically, the effective cataract-inhibiting amount is about 0.01 g to about 0.05 g.

As used herein, the term "effective presbyopia-inhibiting amount" means an amount which will reduce a symptom of presbyopia in an eye or inhibit the progression of additional symptoms of presbyopia in the eye. The effective presbyopia-inhibiting amount of the $\beta_L$-crystallin electrostatic interaction inhibitor will depend on various factors known to those of ordinary skill in the art. Such factors include, but are not limited to, the size of the eye, the number and type of symptoms already present in the individual, and the mode of administration. The effective cataract-inhibiting amount will also depend on whether the pharmaceutical composition is to be administered a single time, or whether the pharmaceutical composition is to be administered periodically, over a period of time. The period of time may be any number of days, weeks, months, or years. In one embodiment, the effective presbyopia-inhibiting amount of the $\beta_L$-crystallin electrostatic interaction inhibitor is about 0.001 g to about 0.1 g. Specifically, the effective presbyopia-inhibiting amount is about 0.01 g to about 0.05 g.

As used herein the term "ophthalmic composition" refers to a pharmaceutically acceptable formulation, delivery device, mechanism or system suitable for administration to the eye. The term "ophthalmic compositions" includes but are not limited to solutions, suspensions, gels, ointments, sprays, depot devices or any other type of formulation, device or mechanism suitable for short term or long term delivery of $\beta_L$-crystallin electrostatic interaction inhibitors to the eye. In contrast to oral formulations, for example, ophthalmic compositions exhibit specific technical characteristics associated with their application to the eyes, including the use of pharmaceutically acceptable ophthalmic vehicles that avoid inducing various reactions such as, for example, irritation of the conjunctiva and cornea, closure of the eyelids, secretion of tears and painful reactions. Specific ophthalmic compositions are advantageously in the form of ophthalmic solutions or suspensions (i.e., eye drops), ophthalmic ointments, or ophthalmic gels containing $\beta_L$-crystallin electrostatic interaction inhibitors. Depending upon the particular form selected, the compositions may contain various additives such as buffering agents, isotonizing agents, solubilizers, preservatives, viscosity-increasing agents, chelating agents, antioxidizing agents, and pH regulators.

Examples of suitable preservatives include, but are not limited to chlorobutanol, sodium dehydroacetate, benzalkonium chloride, cetyl pyridinium chloride, phenethyl alcohol, parahydroxybenzoic acid esters, benzethonium chloride, hydrophilic dehalogenated copolymers of ethylene oxide and dimethyl ethylene-imine, mixtures thereof, and the like. The viscosity-increasing agents may be selected, for example, from methylcellulose, hydroxyethylcellulose, carboxymethylcellulose, hydroxypropylmethylcellulose, polyvinyl alcohol, carboxymethylcellulose, chondroitin sulfate, and salts thereof. Suitable solubilizers include, but are not limited to, polyoxyethylene hydrogenated castor oil, polyethylene glycol, polysorbate 80, and polyoxyethylene monostearate. Typical chelating agents include, but are not limited to, sodium edetate citric acid, salts of diethylenetriamine pentaacetic acid, diethylenetriamine pentamethylenephosphonic acid, and stabilizing agents such as sodium edetate and sodium hydrogen sulfite.

Useful buffers include, but are not limited to borate buffers, phosphate buffers, carbonate buffers, acetate buffers and the like. The concentration of buffer in the ophthalmic compositions may vary from about 1 mM to about 150 mM or more, depending on the particular buffer chosen.

As used herein, the term "vehicle" is intended to include a carrier, diluent or excipient suitable for ophthalmic use.

"Excipient" refers to an ingredient that provides one or more of bulk, imparts satisfactory processing characteristics, helps control the dissolution rate, and otherwise gives additional desirable characteristics to the compositions. In particular, the excipients are selected such that the ophthalmic composition does not trigger a secretion of tears that will entrain the active ingredient. Acceptable excipients are well known to a person skilled in the art, who will know how to select them depending on the desired formulation.

In one embodiment, the $\beta_L$-crystallin electrostatic interaction inhibitor is administered in the form of an ophthalmic device, such as a contact lens or a punctal plug. Suitable ophthalmic devices included biocompatible devices with a corrective, cosmetic or therapeutic quality.

In one embodiment, the $\beta_L$-crystallin electrostatic interaction inhibitor may be adhered to, incorporated into or associated with a contact lens, optionally as a controlled-release composition. The contact lens may be produced using the known materials, for example hydrogels, silicone hydrogels, silicone elastomers and gas permeable materials such as polymethylmethacrylate (PMMA), methacrylic acid ester polymers, copolymers of oligosiloxanylalkyl(meth)acrylate monomers/methacrylic acid and the like. Specific examples of materials for water-containing soft ophthalmic lens include those described in U.S. Pat. No. 5,817,726, 2-hydroxyethyl methacrylate polymers as described in U.S. Pat. No. 5,905,125, ophthalmic lens materials as described in European Patent Application No. 781,777, the hydrogel lens which is coated with a lipid layer in advance as described in U.S. Pat. No. 5,942,558; all incorporated herein for their teachings regarding contact lenses. Generally used contact lens such as hard or rigid cornea-type lens, and gel, hydrogel or soft-type lens which are produced from the above known materials may be used.

A sustained-release $\beta_L$-crystallin electrostatic interaction inhibitor composition may be produced, for example, by incorporating in, associating with or adhering to the contact lens the $\beta_L$-crystallin electrostatic interaction inhibitor composition according to the known methods for producing the contact lenses with sustained-release drugs as described in U.S. Pat. Nos. 5,658,592; 6,027,745; WO2003/003073; US-2005-0079197, incorporated herein for their teachings regarding contact lenses and sustained release. Specifically, the contact lens may be produced by adhering the $\beta_L$-crystallin electrostatic interaction inhibitor composition to a part of a finely-divided or gel sustained-releasing agent such as polyvinyl pyrrolidone, sodium hyaluronate and the like. In addition, sustained release may be produced by forming a $\beta_L$-crystallin electrostatic interaction inhibitor composition reservoir such as by producing a contact lens from a member which forms a front surface of the lens and a member which forms a rear surface of the lens.

In one embodiment, the $\beta_L$-crystallin electrostatic interaction inhibitor is administered in a punctal plug. As used herein, the term punctal plug refers to a device of a size and shape suitable for insertion into the inferior or superior lacrimal canaliculus of the eye through, respectively, the inferior or superior lacrimal punctum.

The invention is further illustrated by the following non-limiting examples.

EXAMPLES

Materials and Methods
Sample Preparation of the Crystallins:
$\beta_L$-crystallin (C5163 Sigma-Aldrich) and α-crystallin (C4163 Sigma-Aldrich) from a bovine eye lens were stored in a biological freezer. The four stock solutions prepared for these experiments were 2 mg/mL $\beta_L$-crystallin in water, 2 mg/mL $\beta_L$-crystallin in PBS, 2 mg/mL α-crystallin in water, and 0.15M NaCl in water. All water used in these experiments was filtered and deionized. A stock solution of 2 mg/mL $\beta_L$-crystallin in water was prepared by mixing 10 mg of $\beta_L$-crystallin with 5 mL water in a decontaminated 20 mL scintillation vial. A similar procedure was followed to prepare 2 mg/mL α-crystallin in water and 2 mg/mL $\beta_L$-crystallin in PBS.

A dilution of these stock solutions was used to create 2 mL samples of 0.2 mg/mL $\beta_L$-crystallin in water, 0.2 mg/mL α-crystallin in water, 0.2 mg/mL $\beta_L$-crystallin, 0.15M NaCl in water, 0.2 mg/mL $\beta_L$-crystallin, 0.6 mg/mL α-crystallin in water, and 0.2 mg/mL $\beta_L$-crystallin in PBS.

The 20 mL scintillation vials were cleaned by sonication for one hour in an extremely dilute solution of Micro-90 surfactant, (Z281506 Sigma-Aldrich) and then rinsed with filtered deionized water eight times and subsequently cleansed with acetone eight times. The crystalline concentrations were verified using an Agilent 8453 UV spectrophotometer equipped with ChemStation software. The molar absorptivity of α-crystallin and $\beta_L$-crystallin at 280 nm is 0.75 and 1.3, respectively.

For the pH study, the 2 mg/mL $\beta_L$-crystallin in PBS stock solution was used to create the samples tested. HCl and NaOH served to mediate the pH. The pH was checked periodically to ensure a stable reading.

Dynamic Light Scattering Background:

Dynamic light scattering, (DLS), is ideal for studying the aggregation mechanisms of the lens as it allows for the Brownian motion of the system to be closely monitored on the molecular level. Using DLS, the native conformation and size of the crystallins in solution can be determined. One of the limits of DLS is that the solution must follow the Zimm regime and thereby have a measured scattering intensity in the range of $qR_g<1$ and a concentration below the overlap concentration, ($c^*$).

$$c^* = \frac{3M_w}{4\pi N_A R_g^3} \qquad (1)$$

An ALV instrument with an Ar laser (λ=514.5 nm) was used to collect DLS data from 35°-65° in 5° increments and from 70°-90° in 10° increments. An ALV5000 correlator was used to analyze the data. Glass DLS tubes (4 mL) were sonicated in an extremely dilute solution of Micro-90 for 1 hour and then rinsed with filtered deionized water eight times followed by acetone eight times. The concentration of crystallins in the lens is typically very high. However, dilute solutions of the crystallins are required for DLS characterization, as set forth by limitations imposed by the Zimm regime. Hence, a 0.2-0.6 mg/mL crystallin solution was injected into the decontaminated DLS tubes.

DLS collects information about the Brownian motion of polymer solutions by monitoring real-time fluctuations in the concentration. During this process, the auto-correlation function of the scattered intensity, I(q,t), is determined using Eq. (2), where q is the scattering wave vector.

$$\frac{<I(q,t)\cdot I(q,t+\tau)>}{<I^2>} = g_2(\tau) \qquad (2)$$

Data collected by the ALV instrument gives $g_2(\tau)$. Then, Contin analysis converts the auto-correlation function into a probability distribution function. This is accomplished by solving for $g_1(\tau)$ using Eq. 3, $$g_2(\tau)=1+|g_1(\tau)|^2 \quad (3)$$

where $g_1(\tau)$ is the Laplace transform of the distribution function $F(\Gamma)$. $\Gamma$ is the inverse of the correlation time, $\tau$. $\Gamma$ can be related to the diffusion coefficient, D, using Eq. (4) so long as $\Gamma$ is experimentally shown to follow a linear $q^2$ dependence.

$$\Gamma=Dq^2 \quad (4)$$

The hydrodynamic radius, $R_h$, can be determined using the Stokes-Einstein equation, $$D = \frac{k_B T}{6\pi\eta R_h} \quad (5)$$

In Eq (5): $k_B$ is the Boltzmann constant; T is the temperature in Kelvin; and $\eta$ is the viscosity of the solvent.

Static Light Scattering Background:

The fundamental difference between static light scattering, (SLS) and DLS is that in SLS the time-averaged mean-square concentration fluctuations of the scattered light are reported, whereas DLS analyzes the Brownian motion of the particles. SLS is typically used to determine the radius of gyration ($R_g$), the weight-averaged molecular weight ($M_w$), and the second virial coefficient ($A_2$). When an aggregate is present in solution with $qR_g > 1$, the fractal dimension ($d_f$) can also be determined.

Partitioning Relative Scattering from Multiple Size-Scales:

In the analysis of a monodisperse, homogeneous solution, one narrow peak will appear in the probability distribution function. This singular peak represents one $R_h$ being present within the solution. In the case where two peaks occur for a single polymer solution, the peaks generally represent the individual chain and aggregate forms of the polymer in solution. When multiple size-scales occur within a solution, the relative intensity can be determined for each size-scale based on the weighted integral of each peak that appears for a particular probability distribution per angle. The first step to determine the relative intensities is to determine the integrals of each peak using equation (6)

$$F(\Gamma)d\Gamma = \int_0^a F(\Gamma)d\Gamma + \int_a^b F(\Gamma)d\Gamma = F_1 + F_2 \quad (6)$$

The integral evaluated from 0 to a represents a fast decay rate and is known as the fast mode. The second integral is called the slow mode and is evaluated from a to b. The integrals of the fast and slow mode are $F_1$ and $F_2$ respectively. If more than two peaks exist, this equation should be modified by adjusting the limits of the integrals and adding additional integrals. Through the determination of $F_1$ and $F_2$ for each angle and application of the relative weight to the static scattering data collected for each angle, $I(q)_{total}$, using equations (7), (8), and (9), the relative scattering intensities for the individual, $I(q)_1$, and aggregates, $I(q)_2$, can be determined.[22]

$$I(q)_{total}=I(q)_1+I(q)_2 \quad (7)$$

$$I(q)_1 = I(q)_{total} \cdot \frac{F_1}{F_1+F_2} \quad (8)$$

$$I(q)_2 = I(q)_{total} \cdot \frac{F_2}{F_1+F_2} \quad (9)$$

Form Factor for $qR_g>1$:

The form factor is defined as the Fourier transform of the monomer density function. This function serves to provide insight into the shape of the polymer system being analyzed. The Debye equation is the form factor for a Gaussian coil.

$$P(q)=2N/(q^4 R_g^4)*[e^{-q^2 R_g^2}-1+q^2 R_g^2] \quad (10)$$

This equation can be further simplified by applying two limits, $qR_g<1$ and $qR_g>1$.

$$\text{For } qR_g<1, P(q)=(1-q^2 R_g^2/3) \quad (11)$$

$$\text{For } qR_g>1, P(q)=2/(q^2 R_g^2) \quad (12)$$

It was stated earlier that $qR_g$ must be less than 1 for the Zimm condition to be true. However, for the experiments discussed herein, in the case of large aggregates with a radius of gyration, $R_g$, greater than 100 nm, this condition is violated. When an aggregate is larger than 100 nm, the scattering intensity includes information about the fractal dimension, polydispersity, and the local monomer density. Of particular interest is the fractal dimension, $d_f$, as it provides some insight into the shape of the aggregate. In order to deduce information about the $d_f$ the relative static intensity data was fitted to the form factor, P(q) in equation (10)

$$P(q)=P(0)*[1+2/(3*d_f)*(qR_g)^2]^{-d_f/2} \quad (13)$$

$$\text{Where, } P(q) \alpha (qRg)^{-df}, qRg<1 \quad (14)$$

Equation (10) was derived based on the conclusion that P(q) for all dimensions is proportional to $N/(qR_g)^{df}$ for $qR_g>1$ of the Debye equation.

The best-fit for $R_g$ and $d_f$ was mathematically determined using a linearized version of equation (13); y=A(1+Bx), where y=$I(q)^{-2/df}$, A=$I(o)^{-2/df}$, B=$(2 R_g^2)/(3 df)$ and x=$q^2$.

Example 1

Characterization of the Crystallins with Dynamic Light Scattering (DLS)

Figure 2:
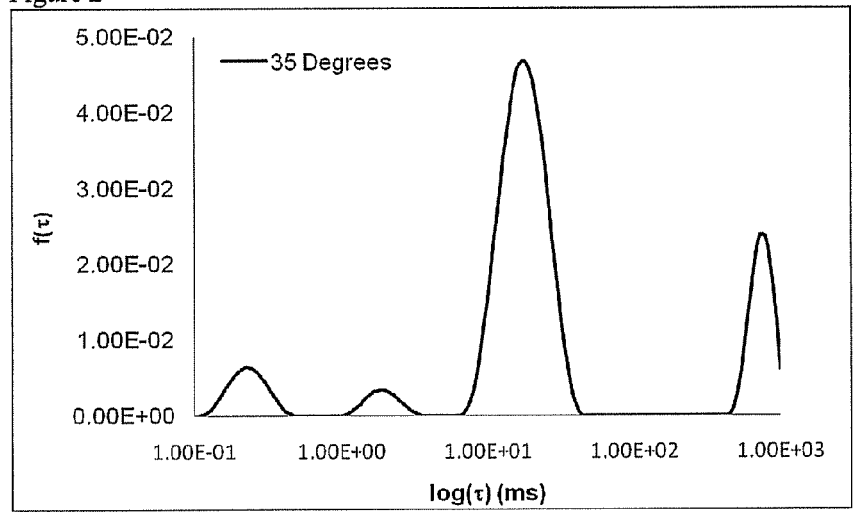
FIG. 2 shows the probability distribution function of 0.2 mg/mL $\beta_L$-crystallin in PBS at 23° C., where τ is the lag time.

By analyzing aggregation trends of the lens crystallins in a dilute solution, the physics of aggregation can be understood. The two proteins analyzed were α-crystallin and $β_L$-crystallin. DLS revealed a solution of 0.2 mg/mL α-crystallin in water at 23° C. to have only one size-scale. A lone $R_h$ of 10 nm was found to be present in solution. The size preference was translated into a single Gaussian peak distribution function, shown in FIG. 1. The proteins with an $R_h$ of 10 nm were seen to have a diffusion coefficient of 2.42e-7 cm$^2$/s. Conversely, when DLS was performed on 0.2 mg/mL $β_L$-crystallin in water at 23° C., two Gaussian peaks appeared in the distribution function. The two peaks represent a fast and a slow mode (FIG. 2). The fast mode is indicative of an individual polymer chain hydrodynamic radius, $R_h$, that is preferred within the solution. The slow mode represents an aggregate $R_h$. The $R_h$ of the fast mode for that sample was 20 nm. The slow mode $R_h$ was beyond the size-scale that can be accurately determined using DLS.

When $\beta_L$-crystallin is in water, a fast and slow mode exists. However, when $\beta_L$-crystallin is placed into phosphate buffered saline solution, PBS, multiple modes exist. Four distinct modes are present in the distribution function of 0.2 mg/mL $\beta_L$-crystallin in PBS. At certain high angles the four modes overlap, so as to appear to be two modes. This is a result of the shifting of these peaks with angle. At low angles, the four peaks are completely resolved, as seen in FIG. 2. The four $R_h$ values that can be found in solution are 1 nm, 4 nm, 97 nm, and a larger size-scale beyond the accurate range of DLS.

Example 2

Fractal Dimension Analysis of $\beta_L$-Crystallin

To understand the shape and size of the aggregates that $\beta_L$-crystallin forms, a fractal dimension analysis was executed on 0.2 mg/mL $\beta_L$-crystallin in water at 23° C. and in PBS at 23° C. The relative scattering intensities due to the individual chain and aggregate were determined for 0.2 mg/mL $\beta_L$-crystallin in water at 23° C. using equations (6)-(9) and then plotted in FIG. 3.

Figure 3:
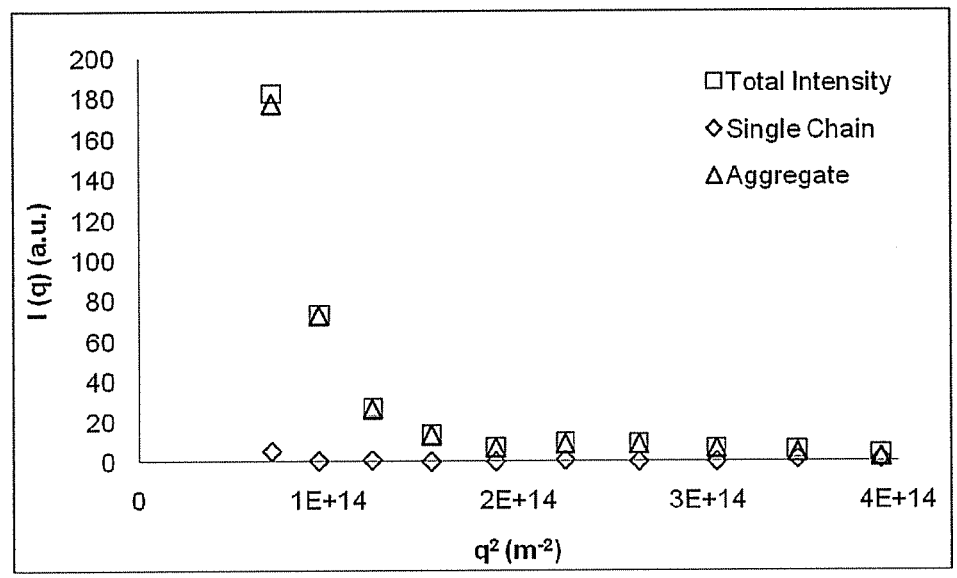
FIG. 3 shows the relative scattered intensity of 0.2 mg/mL $\beta_L$-crystallin in water at 23° C.

FIG. 3 reveals the bulk of the scattering to be due to the aggregate, as expected. This data was used to determine the fractal dimension of the aggregate ($d_f$) with equation (13) by constructing a Kratky plot, which is created by graphing $[I(q)/I(0)]*(qR_g)^2$ versus $qR_g$.

Figure 4:
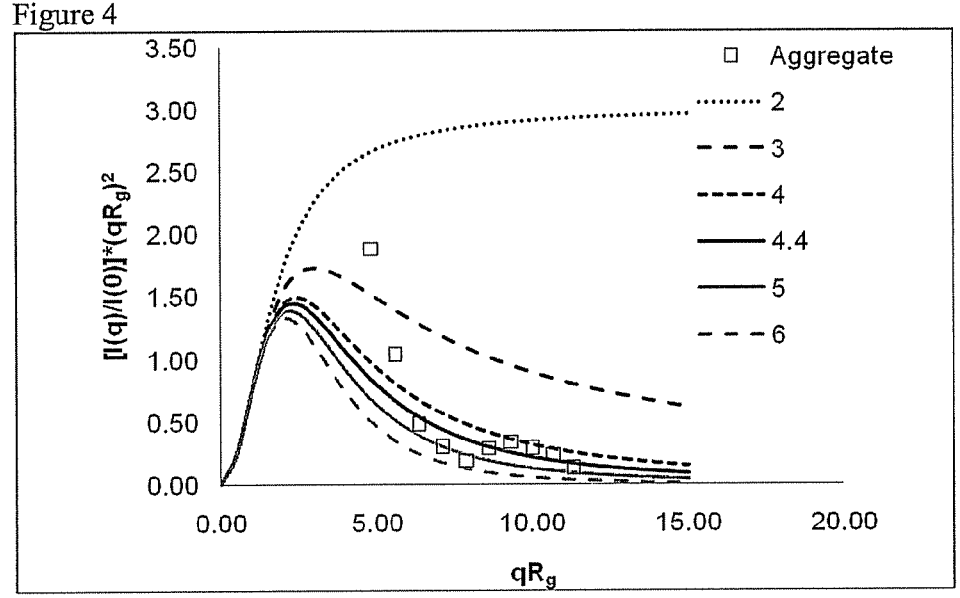
FIG. 4 shows an analysis of the fractal dimension of 0.2 mg/mL $\beta_L$-crystallin in water at 23° C.

According to FIG. 4, the $d_f$ is approximately 4.4. The $R_g$ was determined to be 537 nm, which is on the relative order of what was determined by DLS. It is important to note that the $R_h$ value determined by DLS to be approximately 440 nm may not be accurate due to the limitations of DLS at analyzing size-scales of this magnitude. The data points at the peak on FIG. 4 are considerably shifted to the right and amplified in comparison to the theoretical values. This is most likely due to aggregate polydispersity and aggregate branching.

Figure 5:
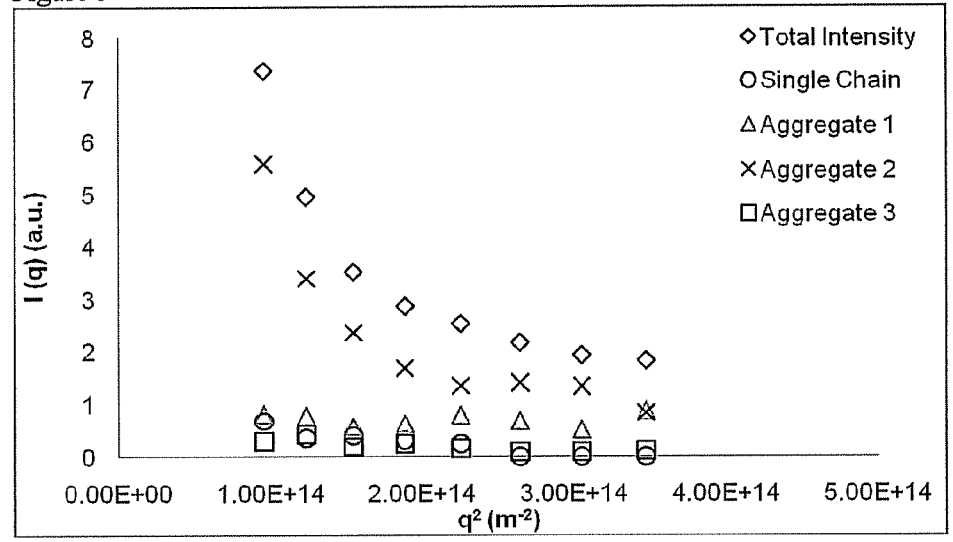
FIG. 5 shows the relative scattered intensity of 0.2 mg/mL $\beta_L$-crystallin in PBS at 23° C.

Although four size-scales were observed when 0.2 mg/mL $\beta_L$-crystallin was in a solution of PBS at 23° C., only one of the peaks fit the criteria to be analyzed with the Kratky plot. The largest aggregate, $R_h \approx 1200$ nm, was the only aggregate that met the $qR_g > 1$ criterion. The relative intensities due to each of the four size-scales were determined using equations (6)-(9), (FIG. 5).

Using equation (13), the $d_f$ for the largest aggregate in 0.2 mg/mL $\beta_L$-crystallin in PBS at 23° C. was determined to be 2.3 by the Kratky plot. The $R_g$ that corresponds to this Kratky plot is 1452 nm, on the order of the $R_h$ at 1200 nm.

Figure 6:
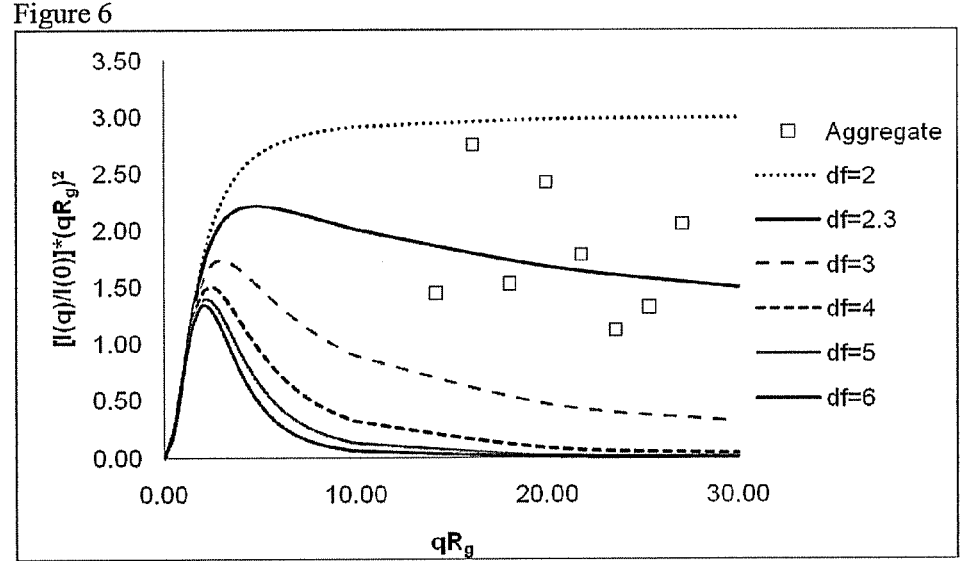
FIG. 6 shows an analysis of the fractal dimension of 0.2 mg/mL $\beta_L$-crystallin in PBS at 23° C.

The data points in FIG. 6 appear to have some margin of error around the theoretical $d_f$ trendline of 2.3. The error is most likely due to the fact that all four of the peaks in the probability distribution functions were not always resolved. This could lead to error in the partitioning of the relative scattered intensity, which would therefore be reflected in the Kratky plot.

Example 3

α-Crystallin's Role as a Chaperone

Figure 7:
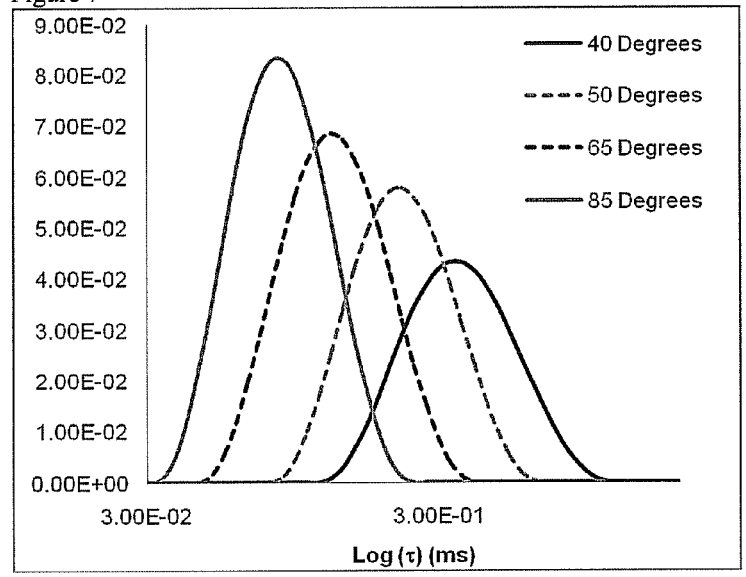
FIG. 7 shows the probability distribution function of 0.2 mg/mL α-crystallin, 0.6 mg/mL $\beta_L$-crystallin in water at 23° C. for angles 40°-85°, where τ is the lag time.

As mentioned earlier, α-crystallin acts as a chaperone protein in the lens as it either diminishes or inhibits aggregation. In order to determine the impact of α-crystallin and its chaperone abilities on $\beta_L$-crystallin, a solution of 0.2 mg/mL $\beta_L$-crystallin, 0.6 mg/mL α-crystallin in water at 23° C. was prepared for DLS. DLS revealed only one peak in the distribution function, (FIG. 7). The addition of the chaperone was thereby seen to remove the aggregate.

Mixtures of α-crystallin in a 3:1 by weight ratio with $\beta_L$-crystallin resulted in suppression of the slow mode. The slow mode is a result of the spontaneous tendency of charged polymers to aggregate in electrolyte solutions. The sizes of the aggregates so formed and their tenuous structures are controllable by the experimental variables determining the strength and range of electrostatic interactions. Since these aggregates scatter light, it is crucial to avoid the formation of such aggregates. This presented a question as to the nature of the interaction between α-crystallin and $\beta_L$-crystallin. Due to the ability of α-crystallin to mediate the aggregation of $\beta_L$-crystallin, it is possible that the aggregation itself is electrostatic in nature.

Example 4

Role of Electrostatics in the Aggregation of $\beta_L$-Crystallin

Figure 8:
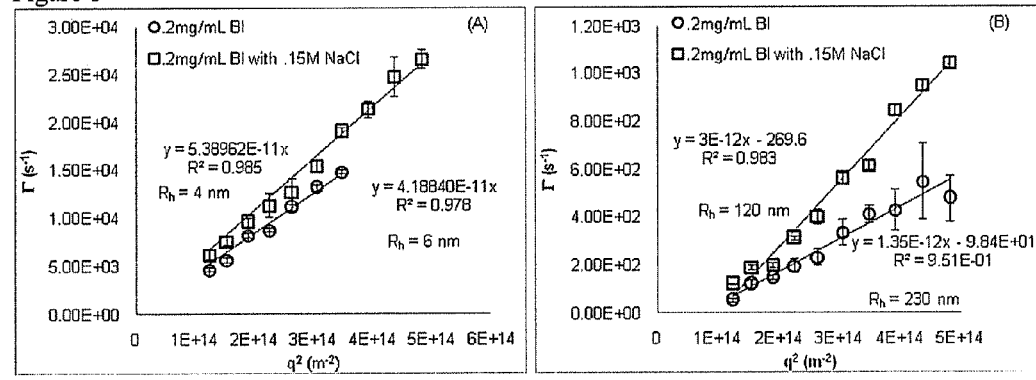
FIG. 8 shows graphs, wherein the slope reveals the hydrodynamic radius of the (A) fast mode with and without 0.15M salt and the (B) slow mode with and without salt of 0.2 mg/mL $\beta_L$-crystallin in water.

In order to determine if the aggregation of the crystallins is electrostatic in nature, dynamic light scattering was accomplished on 0.2 mg/mL $\beta_L$-crystallin in a 0.15M NaCl water solution, (FIG. 8).

The fast mode was not significantly affected by the salt; however the slow mode did change drastically. The addition of the salt caused the aggregate to decrease from a $R_h$ of 230 nm to a $R_h$ of 120 nm. A two-fold reduction in aggregate $R_h$ upon addition of NaCl indicates that the aggregation of the $\beta_L$-crystallin is electrostatic in nature.

Example 5

Kinetic Trends of $\beta_L$-Crystallin in Solution

Aggregation dynamics depend on concentration. Each sample was prepared by diluting a 2 mg/mL stock solution to 0.2 mg/mL. Therefore it was important to define variables to describe the time spent at each of the respective concentrations. The two variables that were used to describe the kinetic trends of $\beta_L$-crystallin were $t_{stock}$ and $t_{tube}$. $t_{stock}$ refers to the time elapsed from the creation of the stock solution to its dilution. $t_{tube}$ is the amount of time elapsed since the DLS tube sample was made by diluting the stock solution. First the kinetic results of $\beta_L$-crystallin in water are discussed and then the results of $\beta_L$-crystallin in PBS are reviewed.

Figure 9:
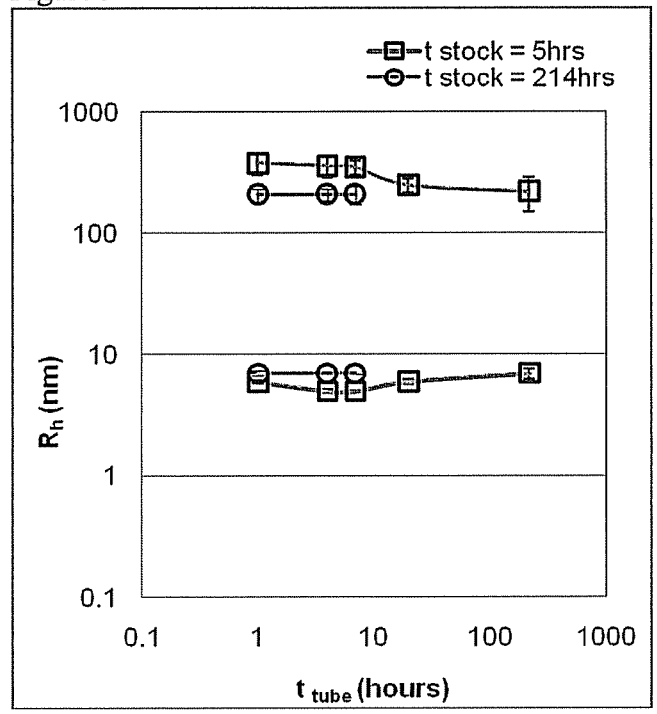
FIG. 9 shows a kinetic study of 0.2 mg/mL $\beta_L$-crystallin in water at 23° C.

DLS was performed on samples of 0.2 mg/mL $\beta_L$-crystallin in water at room temperature at $t_{stock}$ values of 5 hours and 214 hours. These $t_{stock}$ values were chosen to represent a short and a long amount of time in reference to shelf-life and mixing. DLS was run on each sample at a $t_{tube}$ time of 1, 4, 7, 24, and 214 hours. The effect of varying $t_{stock}$ was found to be significant for both the fast and slow modes (FIG. 9).

As equilibrium was not immediately achieved for the system with a $t_{stock}$ of 5 hours, the dynamics of aggregation for 0.2 mg/mL $\beta_L$-crystallin in water is concentration dependent. The 0.2 mg/mL $\beta_L$-crystallin solution at room temperature achieved a stable state with a $t_{stock}$ of 5 hours and a $t_{tube}$ of 100 hours. The hydrodynamic radius for aggregates was also found to reach equilibrium at each $t_{tube}$ value tested for the $t_{stock}$ time of 214 hours. The equilibrium $R_h$ values for the fast and slow modes were 7 nm and 210 nm, respectively.

Figure 10:
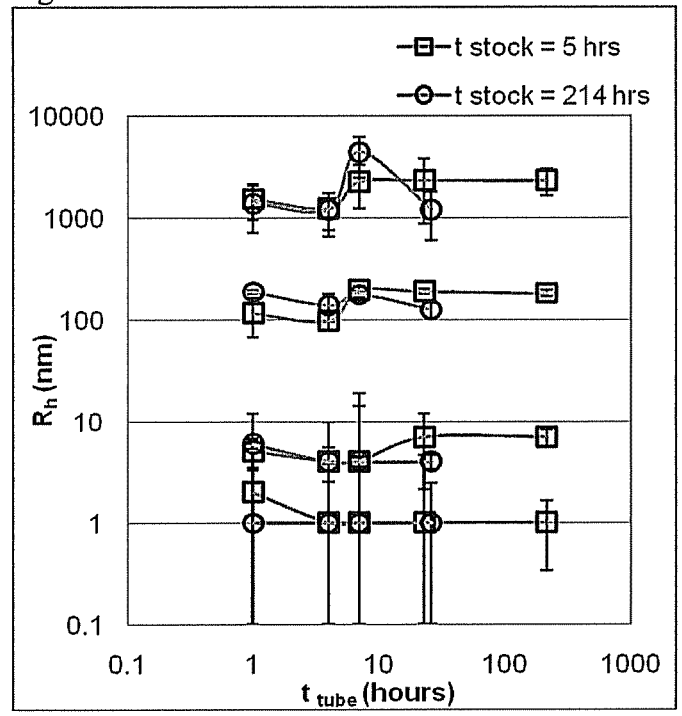
FIG. 10 shows a kinetic study of 0.2 mg/mL $\beta_L$-crystallin in PBS at 23° C.

The kinetics of 0.2 mg/mL $\beta_L$-crystallin in phosphate buffered saline (PBS), 10× (Fisher Scientific) are shown in FIG. 10. Four different size distributions of $\beta_L$-crystallin aggregates were observed in the buffered solution at room temperature using DLS. Once again, $t_{stock}$ values of 5 hours and 214 hours were used. The samples were analyzed using DLS at $t_{tube}$ values of 1, 4, 7, 24, and 214 hours. According to FIG. 10 the hydrodynamic radii remained constant independent of concentration. Therefore, the aggregation state of 0.2 mg/mL $\beta_L$-crystallin in PBS was not seen to be a kinetic process at the time scales measured.

Example 6

Effect of pH Variance on $\beta_L$-Crystallin

Within the functional eye, changes in pH can affect the aggregation state of the crystallins. In this section, the role of pH on aggregation of $\beta_L$-crystallin within the lens is explored. The pH was mediated through titration with HCl and NaOH. The pH values of 2, 4.8, 6, 7, 8, and 10 were examined at 23° C., (Table 1).

TABLE 1

Measured hydrodynamic radius $R_h$ for 0.2 mg/mL $\beta_L$-crystallin in PBS 23° C.; pH is mediated with HCl and NaOH

| Sample pH | $R_h$ | $R_h$ | $R_h$ | $R_h$ |
|---|---|---|---|---|
| 2 | 2 nm | | | 4.5 μm |
| 4.8 | | | | 4.6 μm |
| 6 | | | 614 nm | |
| 7 | 2 nm | 8 nm | 165 nm | 2.2 μm |
| 8 | | | | 1.4 μm |
| 10 | | | 91 nm | 1.4 μm |

Figure 11:
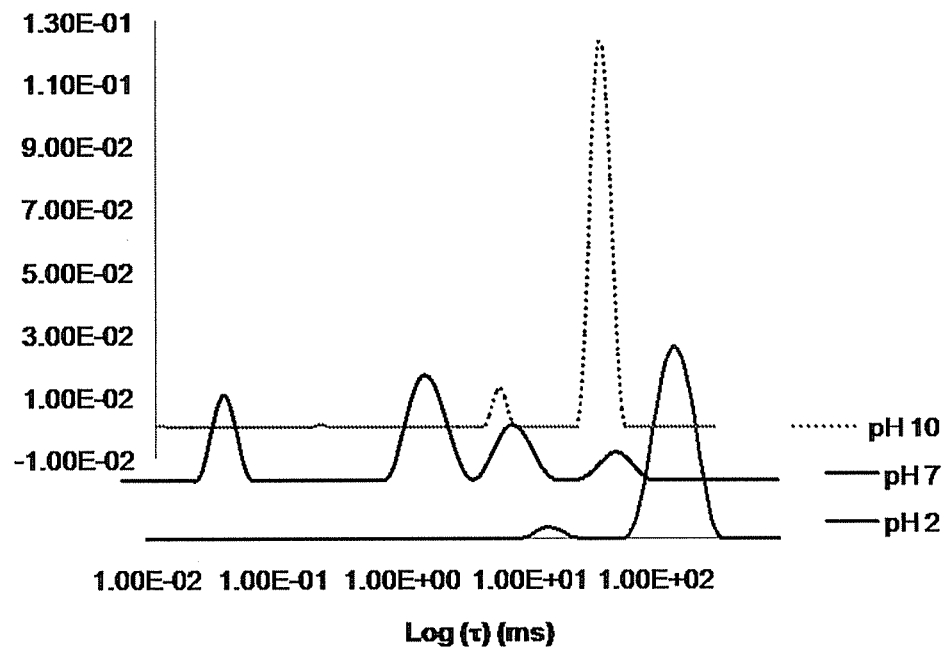
FIG. 11 shows a probability distribution function of pH of 2, 7, and 10 for 0.2 mg/mL $\beta_L$-crystallin in PBS at 23° C.

At all pH values other than physiological pH, a fast and slow mode exists in dynamic light scattering. Each mode represents a particular size of the scattering entity. The fast mode represents unaggregated molecules and the slow mode represents aggregated structures. Under the most acidic (pH=2) and basic (pH=10) conditions, the largest size scale dominated the data, however a second size scale was clearly present. This conclusion was drawn based on the relative integrals of the two peaks in the probability distribution function, (FIG. 11). The sizes and the propensity of the clumped protein aggregates clearly depend on the pH, demonstrating the role of electrostatics.

Figure 12:
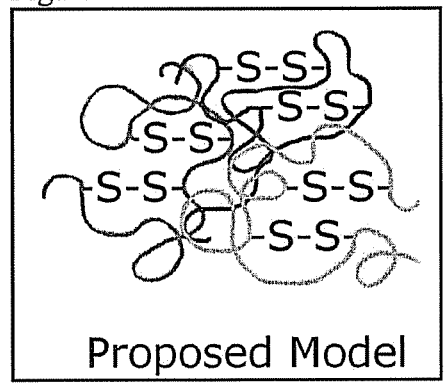
FIG. 12 is an illustration of the proposed mechanism of cataract formation.

Considering the findings about the nature of crystallins in different solutions and role of electrostatics, it is proposed herein that the intermolecular disulfide bonds previously believed to cause the aggregation found in cataracts are intramolecular. FIG. 12 depicts an illustration of the proposed model.

Example 7

SDS and Proteoglycan Do Not Deaggregate $\beta_L$-crystallin

Figure 13:
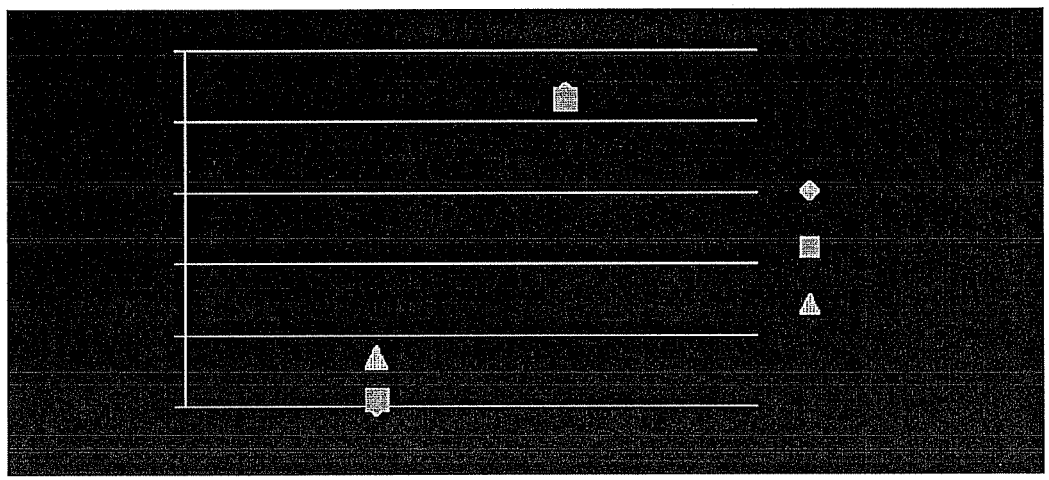
FIG. 13 shows graphs that reveal the hydrodynamic radius of the fast mode and the slow mode with and without SDS of 0.2 mg/mL $\beta_L$-crystallin in water.

The effect of SDS, sodium dodecyl sulfate (purchased from Sigma Aldrich) a nonionic surfactant on $\beta_L$-crystallin deaggregation was studied as in Example 4. The CMC for SDS is 2.36 mg/ml, so the SDS concentration was maintained below that value. As shown in FIG. 13, SDS did not stimulate de-clumping of $\beta_L$-crystallin.

A proteoglycan is made up of keratin sulfate, chondroitin sulfate and hyaluronic acid. Addition of proteoglycan to $\beta_L$-crystallin resulted in an increase in aggregate size as shown in Table 2:

TABLE 2

| [proteoglycan] | $\beta_L$-crystallin | $R_h$ | $R_h$ | $R_h$ | $R_h$ | $R_h$ |
|---|---|---|---|---|---|---|
| 0 | 0.2 mg/mL | | 11 nm | 63 nm | | |
| 0.1 mg/mL | 0.2 mg/mL | 4 nm | 21 nm | 150 nm | 641 | 6000 |

Proteoglycan increases the $\beta_L$-crystallin size.

Example 8

Effect of pH on $\beta_L$-crystallin Aggregate Size

The aggregation phenomena of $\beta_L$-crystallin were used as a model for understanding the physics of aggregation involved in cataract formation. The initial analysis of the system showed that α-crystallin formed a one distribution peak system, representative of one hydrodynamic radius, $R_h$, in solution. $\beta_L$-crystallin had a fast and slow mode in water and four size scales in PBS. The fast mode corresponds to isolated molecules and the slow mode corresponds to the aggregates. The fractal dimension of the largest aggregates in both water and PBS was studied by fitting the scattered intensity with the form factor for fractal objects. The interaction between α-crystallin and $\beta_L$-crystallin was then studied, or more specifically, the chaperone nature of α-crystallin. α-crystallin was demonstrated to reduce the clumping of $\beta_L$-crystallin when added to a solution of $\beta_L$-crystallin. The effect of reducing the aggregate was then observed by using 0.15M NaCl instead of the α-crystallin. This experiment demonstrated the clumping of $\beta_L$-crystallin to be electrostatic in nature.

The kinetics of aggregation was studied in both water and PBS at 23° C., by monitoring the scattered intensity and its correlations as functions of time over two weeks. The $R_h$ values for 0.2 mg/mL $\beta_L$-crystallin in water required approximately 2 weeks to reach equilibrium. Therefore, it was determined that equilibrium for these solutions would be achieved on a time scale that would impact experiments. The $R_h$ values for 0.2 mg/mL $\beta_L$-crystallin in PBS reached equilibrium within a few minutes.

The pH was mediated for a solution of 0.2 mg/mL of $\beta_L$-crystallin in PBS at 23° C. Biological conditions resulted in wide range of $R_h$ values existing in solution. However, when the pH was pushed to the acidic (4.8) or basic (8-10) regimes, one aggregate size-scale dominated the solution. The series of experiments discussed, namely variations in the composition of $\beta_L$-crystallin and α-crystallin, PBS buffer versus water, pH, temperature, presence of SDS, and salt concentration have demonstrated the considerable impact environmental changes can have on the aggregation of $\beta_L$-crystallin.

Due to the significant role that electrostatics has been determined to play in the clumping of $\beta_L$-crystallin, it is suggested herein that the aggregation mechanism of cataracts themselves are in fact also dominated by electrostatics. Therefore, our results offer a strategy to mitigate the forces responsible for the aggregation of $\beta_L$-crystallin and the occurrence of cataract by deliberately interfering with the electrostatic forces.

Ionic liquids satisfy two requirements to break up the electrostatic correlations of the aggregating monomers. The chemical structure of ionic liquids is a composite of a hydrophobic part and an ionic part. The ionic parts mediate the electrostatic interactions between the protein monomers. At the same time, these smaller ions are placed in the vicinity of the protein molecules by anchoring the hydrophobic tails of these ions. In addition, the shorter tail lengths of these ions prevent them from phase separating away from the proteins as would happen in oil-water solutions.

The terms "a" and "an" do not denote a limitation of quantity, but rather denote the presence of at least one of the referenced item. The term "or" means "and/or". The terms "comprising", "having", "including", and "containing" are to be construed as open-ended terms (i.e., meaning "including, but not limited to").

Embodiments are described herein, including the best modes known to the inventors. Variations of such embodiments will become apparent to those of ordinary skill in the art upon reading the foregoing description. The skilled artisan is expected to employ such variations as appropriate, and the disclosed methods are expected to be practiced otherwise than as specifically described herein. Accordingly, all modifications and equivalents of the subject matter recited in the claims appended hereto are included to the extent permitted by applicable law. Moreover, any combination of the above-described elements in all possible variations thereof is encompassed unless otherwise indicated herein or otherwise clearly contradicted by context.

The invention claimed is:

1. A method of inhibiting or reversing in situ the progression of cataract formation in an eye comprising
    contacting the crystalline lens in situ in the eye with an effective cataract-inhibiting amount of an ophthalmic composition comprising at least one $\beta_L$-crystallin electrostatic interaction inhibitor, wherein the $\beta_L$-crystallin electrostatic interaction inhibitor is an organic or inorganic salt selected from $NH_4Cl$, $CaCl_2$, sodium acetate, potassium acetate, ammonium acetate, sodium citrate, potassium citrate, ammonium citrate, sodium sulphate, potassium sulphate, ammonium sulphate, calcium acetate, ethylammonium nitrate, sodium formate, sodium ascorbate, magnesium gluconate, sodium gluconate, tromethamine hydrochloride, sodium succinate, and combinations thereof.

2. A method of inhibiting or reversing the progression of cataract formation in an eye comprising
    contacting the eye with an effective cataract-inhibiting amount of an ophthalmic composition comprising at least one $\beta_L$-crystallin electrostatic interaction inhibitor, wherein the $\beta_L$-crystallin electrostatic interaction inhibitor comprises an organic salt containing a cation and an anion, wherein the cation and the anion are each independently an aliphatic group with the length of the aliphatic moiety of four to fifteen carbon atoms.

3. The method of claim 2, wherein the organic salt comprises an ionic liquid.

4. The method of claim 1, wherein the $\beta_L$-crystallin electrostatic interaction inhibitor is in the form of an ophthalmic composition comprising at least one ophthalmically acceptable vehicle.

5. The method of claim 4, wherein the ophthalmic composition is an eye drop.

6. The method of claim 4, wherein the ophthalmic composition is an ophthalmic device.

7. The method of claim 6, wherein the ophthalmic device is a contact lens or a punctal plug.

8. The method of claim 2, wherein the $\beta_L$-crystallin electrostatic interaction inhibitor is in the form of an ophthalmic composition comprising at least one ophthalmically acceptable vehicle.

9. The method of claim 8, wherein the ophthalmic composition is an eye drop.

10. The method of claim 8, wherein the ophthalmic composition is an ophthalmic device.

11. The method of claim 10, wherein the ophthalmic device is a contact lens or a punctal plug.

12. The method of claim 3, wherein the $\beta_L$-crystallin electrostatic interaction inhibitor is in the form of an ophthalmic composition comprising at least one ophthalmically acceptable vehicle.

13. The method of claim 12, wherein the ophthalmic composition is an eye drop.

14. The method of claim 12, wherein the ophthalmic composition is an ophthalmic device.

15. The method of claim 14, wherein the ophthalmic device is a contact lens or a punctal plug.

16. The method of claim 3, wherein the ionic liquid is an N'-alkyl or N'-(ω-hydroxy-alkyl)-N-methylimidazolium chloride, a tri-isobutyl(methyl) phosphonium p-toluenesulfonate, a 1-ethyl-3-methylimidazolium tetrafluoroborate, a 1-butyl-3-methylimidazolium chloride, a 1-hexyl-3-methylimidazolium chloride, a 1-ethyl-3-methylimidazolium trifluoromethanesulfonate, a 1-ethyl-3-methylimidazolium trifluoromethanesulfonate, a tetraethylammonium bromide, an n-butylpyridinium chloride, a tetrabutylphosphonium bromide, a benzyltriethylammonium chloride, a 1-ethyl-3-methylimidazolium chloride, a 1-butyl-2,3-dimethylimidazolium tetrafluoroborate, a 1,3-dimethylimidazolium methyl sulfate, a 1-butyl-3-methylimidazolium trifluoroacetate, a 1-butyl-3-methylimidazolium chloride, a 1-butyl-3-methylimidizolium 2(2-methoxyethoxy)ethylsulfate, a 1-butyl-1-methylpyrrolidinium dihydrogenphosphate, or a combination thereof.

* * * * *